(12) United States Patent
Wong

(10) Patent No.: US 6,468,558 B2
(45) Date of Patent: Oct. 22, 2002

(54) LIPOSOME-ENCAPSULATED POLY ICLC

(75) Inventor: Jonathan P. H. Wong, Medicine Hat (CA)

(73) Assignee: Her Majesty the Queen in right of Canada, as represented by the Minister of National Defence of Her Majesty's Canadian Government, Ottawa (CA)

( * ) Notice: Subject to any disclaimer, the term of this patent is extended or adjusted under 35 U.S.C. 154(b) by 0 days.

(21) Appl. No.: 09/981,838

(22) Filed: Oct. 19, 2001

(65) Prior Publication Data

US 2002/0086050 A1 Jul. 4, 2002

Related U.S. Application Data

(63) Continuation of application No. 09/270,746, filed on Mar. 16, 1999, now abandoned, which is a continuation of application No. 09/065,553, filed on Apr. 24, 1998, now abandoned.

(30) Foreign Application Priority Data

Apr. 28, 1997 (CA) .............................................. 2203843

(51) Int. Cl.$^7$ ............................................... A61K 9/127
(52) U.S. Cl. ........................................ 424/450; 514/888
(58) Field of Search ............................. 424/450, 78.08, 424/78.36; 514/44, 54, 888, 889

(56) References Cited

U.S. PATENT DOCUMENTS

| | | |
|---|---|---|
| 4,897,355 A | 1/1990 | Eppstein |
| 5,763,417 A | 6/1998 | Einck |

OTHER PUBLICATIONS

Salazar Neurosurgery 1996, 38:1096–1104 Long–term treatment of malignant gliomas with intramuscularly etc.

Wong et al Antimicrobial Agents and Chemotherapy Nov. 1995, p. 2574–2576 vol. 39, No. 11 Prophylactic and Therapeutic Efficacies of Poly (IC•LC) against Respiratory Influenza A Virus Infection in Mice etc.

Baer et al J. of Infectious Diseases vol. 136, No. 2, Aug. 1977, p. 286–292 Successful Prophylaxis against Rabies in Mice and Rhesus Monkeys: The Interferon System and Vaccine.

Kende J. of Biological Response Modifiers 4:503–511, 1985 Propylactic and Therapeutic Efficacy of Poly etc.

Levin et al Cancer Treatment Reports vol. 62, No. 11, Nov. 1978 Phase I–II Trials of Poly IC Stabilized etc.

Stephen et al J. of Infectious Diseases vol. 139, No. 3, Mar. 1979 p. 267–272 Protective and Toxic Effects of a Nuclease–Resistant Derivative of Polyriboinosinic–Polyribocytidylic Acid on Venezuelan Equine etc.

Ostro in Amer. J. of Hospital Pharmacy 46, Aug. 1989, p. 1576.

(List continued on next page.)

Primary Examiner—Gollamudi S. Kishore
(74) Attorney, Agent, or Firm—Nixon & Vanderhye P.C.

(57) ABSTRACT

Although poly ICLC possess a broad spectrum of antimicrobial and anticancer activities, it therapeutic potential has yet to be fulfilled due to its toxic side effect. This problem can be overcome by encapsulating poly ICLC within liposomes which provides a drug delivery system with slow sustained release characteristic and which has the ability to target the drug to sites of infection and tumor without causing systemic burden to normal tissues, thereby enhancing the immunological and biological activities of poly ICLC.

18 Claims, 2 Drawing Sheets

OTHER PUBLICATIONS

Levine et al., "Phase I–II Trials of Poly IC Stabilized with Poly–L–Lysine", Cancer Treatment Reports, vol. 62, No. 11, Nov. 1978, pp. 1907–1912.

Theriault et al., "Evaluation of Polyinosinic–Polycytidylic and Poly–L–lysine in Metastatic Breast Cancer", Cancer Treatment Reports, vol. 70, No. 11, Nov. 1986, pp. 1341–1342.

Droller, "Immunotherapy of Metastatic Renal Cell Carcinoma with Polyinosinic–Polycytidylic Acid", The Journal of Urology, vol. 137, Feb., 1986, pp. 202–206.

Stevenson et al., "A Phase I Evaluation of Poly(I,C)–LC in Cancer Patients", Journal of Biological Response Modifiers, vol. 4, No. 6, 1985, pp. 650–655.

Maluish et al., "Immunomodulatory Effects of Poly(I,C)–LC in Cancer Patients", Journal of Biological Response Modifiers, vol. 4, No. 6, 1985, pp. 656–663.

LIPOSOME-ENCAPSULATED POLY ICLC

This application is a continuation of application Ser. No. 09/270,746, filed Mar. 16, 1999, now abandoned which is a continuation of application Ser. No. 09/065,553, filed Apr. 24, 1998, now abandoned the entire content of which is hereby incorporated by reference in this application.

FIELD OF THE INVENTION

The present invention relates to a poly ICLC formulation with improved therapeutic efficacy.

BACKGROUND OF THE INVENTION

Double-stranded RNAs (dsRNAs) are very potent biologic modifiers. They can exert a profound influence on cells at nanomolar concentrations. The modulating effects of dsRNA include a broad spectrum of actions at the molecular and cellular levels. At the molecular level, dsRNAs can elicit biological effects such as interferon synthesis, induction of protein kinase, induction of 2–5A polymerase. enhancement of histocompatibility antigen and inhibition of metabolism. And at the cellular level, dsRNA can elicit biological effects such as pyrogenicity, mitogenicity, macrophage activation, activation of cell-mediated immunity and induction of antiviral state. One promising potential of dsRNAs is its immunomodulating effect in antimicrobial and anticancer therapies. In particular, the double-stranded RNA poly ICLC, or PICLC for short, was found highly effective as an antiviral or antitumor agent.

Poly ICLC is a synthetic dsRNA consisting of polyriboinosinic and polyribocytidylic acid strands (poly I.poly C) stabilized with poly-L-lysine and carboxymethylcellulose. The resulting poly ICLC is thermodynamically more stable than poly I.poly C. Poly ICLC has been shown in clinical trials to be effective in the cancer treatment of gliomas (Salazar, A, M. & al., Neurosurgery 38:1096–1104). It has also been shown in a number of studies to be effective in the immunotherapy of viral infection including influenza (Wong, J. P. Antimicrob. Agents Chemother, 39:574–2576), rabies (Baer, G. M., J. Infect. Dis. 136:286–292). Rift Valley fever (Kende, M., J. Biol. Response Modifiers 4:503–511) and Venequelan equine encephamyelitis (Stephen, E. L., J. Infect. Dis. 136:267–272).

Although poly ICLC is a promising immunomodulator which has great potential in antimicrobial and anticancer therapies, it has been shown to produce serious side effects in humans, especially when the drug is administered in multiple high doses. Some of the reported side effects (Levine, A. S., Cancer Treat. Rep. 62:1907–1913) include fever, hypotension, leukopenia, myalgia, thrombocytopenia and poly arthalgia. The inherent toxicity problem must be overcome to render poly ICLC safer for use in humans. Furthermore, the therapeutic efficacy of poly ICLC is limited by its stability in vivo. As a ribonucleic acid, poly ICLC is susceptible to degradation in the body by serum RNAse. Although the extent of RNAse degradation of poly ICLC is much improved as compare to that of poly I.poly C, the protection is not complete and poly-L-lysine and carboxymethylcellulose themselves may be susceptible to enzymatic degradation and immunological clearance in vivo. Therefore, a need exists for an improved formulation of poly ICLC which has improved therapeutic efficacy and will be safer for use in humans.

SUMMARY OF THE INVENTION

It is an object of the present invention to provide a poly ICLC formulation having enhanced therapeutic efficacy while reducing it toxic effect in humans.

In accordance with one aspect of the present invention, there is provided an immunomodulating agent comprising poly ICLC encapsulated within liposomes. Preferably, the liposomes used are unilamellar or multilamellar and contain at least one cationic phospholipid such as stearylamine, 1,2-diacyl-3-trimethylammonium-propane (TAP) or 1,2-triacyl-3-dimethylammonium-propane (DAP). Most preferably, the liposomes are unilamellar or multilamellar liposomes prepared from the lipids phosphatidylcholine and stearylamine, and the steroid cholesterol at a molar ratio of approximately 9:1:1, respectively. The surface liposomes may be coated with polyethylene glycol to prolong the circulating half-life of the liposomes, and with antibody for targeting to specific sites in the body.

Neutrally charged liposomes can also be used for liposomal entrapment of poly ICLC. Such neutrally charged liposomes can be prepared by using, for example phosphatidylcholine and cholesterol.

In accordance with another aspect of the present invention there is provided a method for preparing liposomal poly ICLC comprising the step of freeze-drying a mixture of liposomes and poly ICLC. Conveniently, the method includes removing organic solvent from a mixture of phospholipids, rehydrating the resulting lipids mixture with an aqueous buffer containing poly ICLC, freeze-drying the resulting lipid-poly ICLC mixture, reconstituting the resulting dried mixture, and resuspending the resulting liposome pellets with a buffer solution to the desired drug concentration prior to use. Suitable buffer can be phosphate buffered saline, normal saline or deionized water. It is important for the preparation of buffer solution to use RNAse-free water so that enzymatic degradation of poly ICLC can be minimized.

Alternate methods of preparation of liposomes include detergent dialysis, extrusion, reverse-phase evaporation (REV) and sonication. The loading of poly ICLC into the liposomes can be achieved by passive trapping and by active process such as remote loading. The unentrapped poly ICLC can be removed by centrifugation, column separation or by dialysis.

The advantages of encapsulating poly ICLC in liposomes are that the toxicity of poly ICLC is decreased, and at the same time the therapeutic efficacy of poly ICLC is increased. Furthermore, liposomal poly ICLC protects the poly ICLC from RNAse degradation in the body, thereby enhancing the immunological and biological activities of poly ICLC.

DETAILED DESCRIPTION

Poly ICLC

Figure 1:
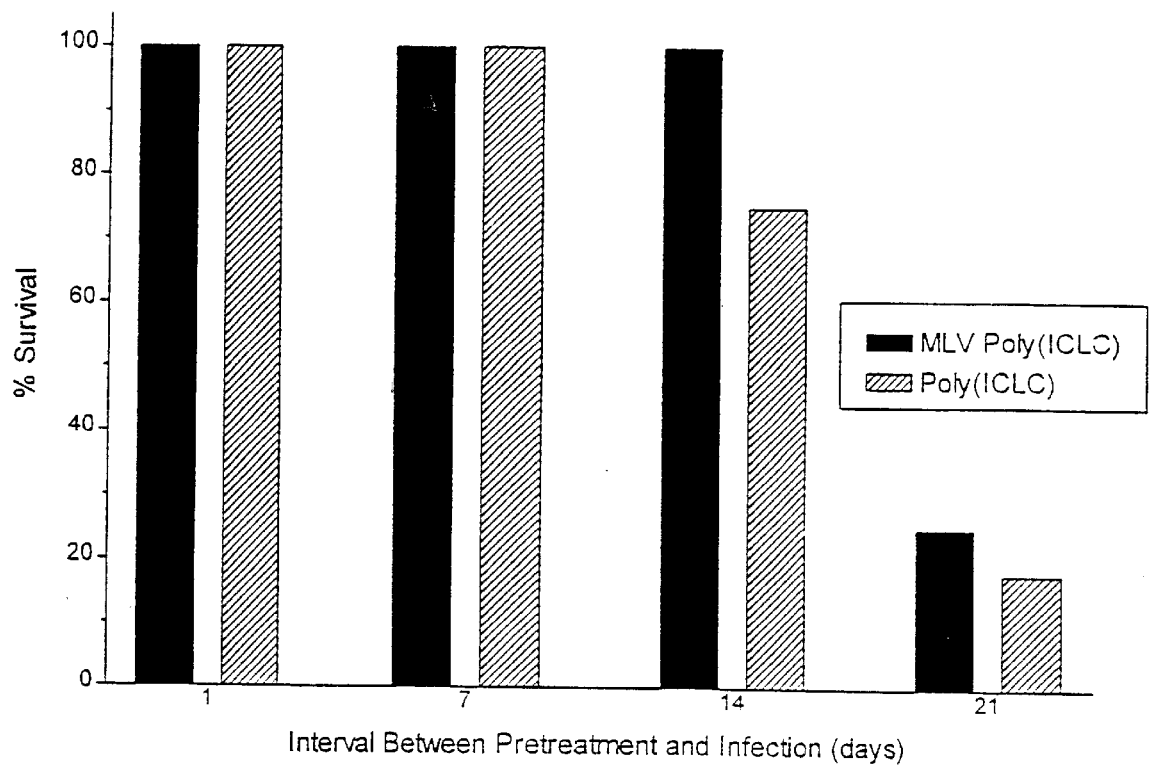
FIG. 1 is a graph showing results of tests relating to the therapeutic efficacy of free poly ICLC versus that of liposomal poly ICLC.

Poly ICLC was prepared by the Pharmaceutical Services, College of Pharmacy University Of Iowa (Iowa City, Iowa.), and was provided by the National Institute of Health (Bethesda, Md.). Each milliliter of poly ICLC contained 2 mg poly I.poly C, 1.5 mg poly-L-lysine, and 5 mg carboxymethylcellulose in 0.9% sodium chloride.

Encapsulated-liposome Poli ICLC

Liposomes are microscopic lipid vesicles consisting of one or more lipid bilayer(s) and aqueous compartment(s).

The primary constituents of liposomes are usually a combination of phospholipids and steroid, such as cholesterol. The phospholipids can be positively, neutrally and negatively charged. Liposomes made from positively and negatively charged phospholipids are called cationic and anionic liposomes, respectively. DNA and RNA are usually negatively charged, therefore, cationic liposomes are the liposomes of choice for making liposomal poly ICLC formulation. The cationic phospholipid used for making liposomal poly ICLC is preferably stearylamine, 1,2-diacyl-3-trimethylammonium-propane (TAP) or 1,2-triacyl-3-dimethylammonium-propane (DAP). Cholesterol is included for stabilization of the bilayer. The surface liposomes may be coated with polyethylene glycol to prolong circulation thereof. Proteins can also be combined with the liposome membranes to promote binding with specific cell receptors.

Liposomes used for entrapment of poly ICLC may be large multilamellar vesicles (MLVs), small unilamellar vesicles (SUVs) or large unilamellar vesicles (LUVs). Preferably, MLVs are used for preparing liposomal poly ICLC.

When used as a drug delivery system, liposomes are known to have a slow sustained release characteristic and the ability to target drugs to sites of infection and tumor without causing systemic burden to normal tissues. Liposomes have been used successfully to entrap a number of therapeutic drugs, including antibiotics, antivirals, and anticancer. Because of these attributes, liposomal poly ICLC is an excellent drug delivery system which can significantly decrease the dose-related toxicity of poly ICLC. Furthermore, liposome-encapsulation protects the poly ICLC from RNAse degradation in the body, thereby enhancing the therapeutic efficacy of poly ICLC.

Preparation

The liposomes were prepared using 210 mg of phosphatidylcholine (210 $\mu$mole), 23.2 mg stearylamine (23.2 $\mu$mole) and 8.1 mg cholesterol (30 $\mu$mole). The lipids were added in a 100 ml round bottom flask, 2 ml of chloroform was added to dissolve the lipids. The round bottom flask was rotary evaporated in a 45° C. water bath until a dried lipid film was formed. The flask was then placed in a vacuum oven (45° C., –80 Kpa) for one hour to remove residual organic solvent. The lipid film was then reconstituted with 3 ml of poly ICLC (2 mg/ml) followed by 3 ml of 0.9% NaCl. Other suitable buffers can be phosphate buffered saline, normal saline or deionized water. It is important for the preparation of buffer solution to use RNAse-free water to minimize degradation of poly ICLC. The lipid-drug mixture was then transferred to a screwcapped tube, mixed well, and frozen by immersing the tube in liquid nitrogen. The sample was then lyophilized overnight until all the liquid was removed to obtain a white dried powder. Following lyophilization, the sample was rehydrated with 100–150 $\mu$l 0.9% NaCl, incubated for 15 min, at 45° C., and left undisturbed for 2 hr. at room temperature. The liposomal poly ICLC was diluted in sterile 0.9% NaCl and washed using an ultracentrifugation step. The liposome pellet was then resuspended with a buffer solution to the desired drug concentration for administration into mice.

The surface of the liposomes may be coated with polyethyleneglycol to prolong circulation and with an antibody to increase the affinity of the liposome to specific sites of infection and tumor.

Neutrally charged liposomes can also be used for liposomal entrapment of poly ICLC. For example, the neutrally charged liposomes can be prepared using phosphatidylcholine and cholesterol.

Other methods of preparation to produce liposomes include detergent dialysis, extrusion, reverse-phase evaporation (REV) and sonication. The loading of poly ICLC into the liposomes can be achieved by passive trapping or by active process, such as remote loading. The unentrapped poly ICLC can be removed by centrifugation, column separation or by dialysis.

Adaptation of Egg-propagated Influenza A/PR/8 Virus in Mice

Figure 2:
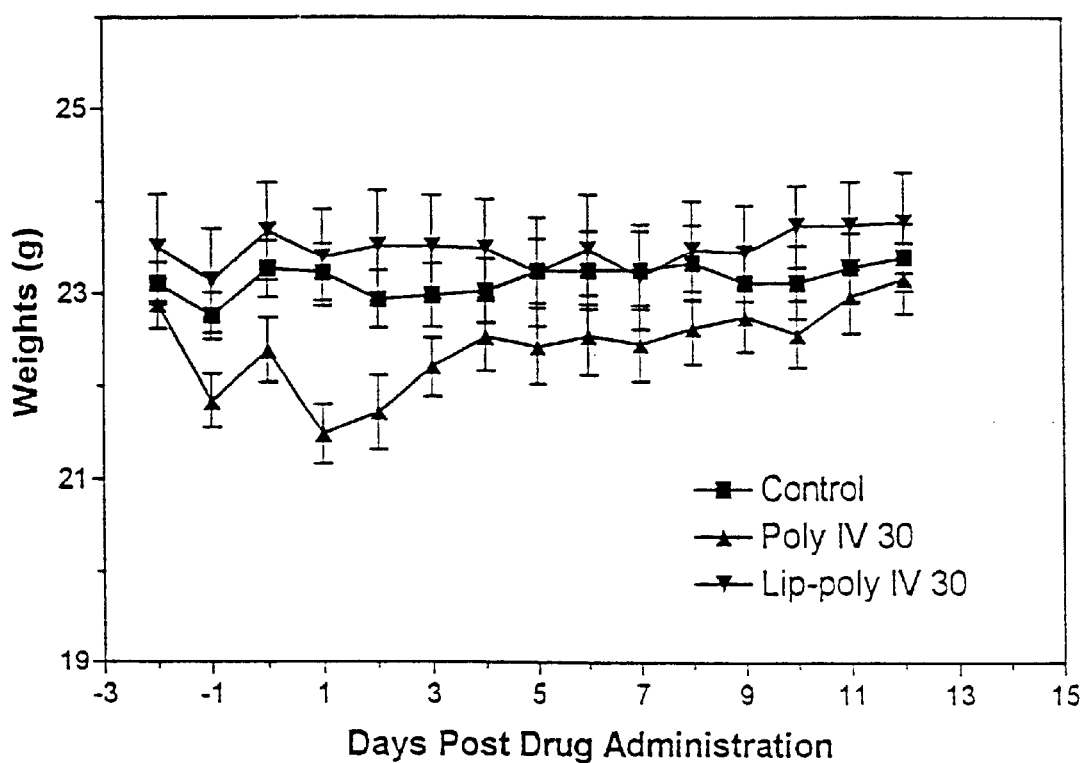
FIG. 2 is a graph showing the results of tests relating to the toxicity of free poly ICLC versus that of liposomal poly ICLC.

Using conventional procedures, influenza A/PR/8 virus was communicated to mice through lung passages by four blind passages utilizing egg-propagated virus (available from ATTC, Parklawn, Md.) as the initial inoculum. The virus became pathogenic in mice as early as the third passage. The symptoms of influenza were standing fur, rapid loss of body weight, grouping together and significant loss of animal's movement inside the cages. Post-mortem examination of the infected mice revealed severe pulmonary lesions and pulmonary enlargement was also observed in some mice.

Testing

Liposome-encapsulated poly ICLC was administered to the mice by intranasal, intraperitoneal or intravenous routes. The volumes of inoculum used were 50 μl for the intranasal route and 100 μl by the intraperitoneal and intravenous routes. For the intranasal and intraperitoneal routes, mice were anaesthetized with sodium pentobarbital prior to administration of the drug. When the animals were unconscious, they were carefully supported by hands with their nose up, and the antiviral agents were gently applied with a micropipette into the nostrils. The applied volume was naturally inhaled into the lungs.

Groups of anesthetized mice (5–10 mice per group) were given one or two doses (20 μg/dose) of poly ICLC or liposome-encapsulated poly ICLC by the intraperitoneal or intravenous route. The doses were given to the mice 7, 14 and 21 days prior to virus challenge. The mice were then intranasally infected with 10 $LD_{50}$ mouse-adapted influenza A/PR/8 virus. At day 14 post virus infection, the number of mice which survived the virus challenged was recorded.

Results

The efficacy of free and liposome-encapsulated poly ICLC for the prophylactic protection of mice against lethal challenges of influenza A infection in mice is shown in FIG. 1. In comparison, mice which were administered free poly ICLC within 7 days prior to virus infection had a 100% survival rate at day 14 post virus infection. However when pretreatment of free poly ICLC were given at days 14 and 21 prior to virus challenge, the survival rates at day 14 post infection decreased. In contrast, mice which were given liposome-encapsulated poly ICLC (MLV poly ICLC) within days 7 and 14 prior to virus challenge had a 100% survival rate at day 14 post virus infection. These results showed that liposome encapsulation did not adversely affect the antiviral and immunomodulating activities of poly ICLC, but, rather enhanced these activities by prolonging the antiviral state.

Referring now to FIG. 2, there is shown the effect of toxicity of free and liposomal poly ICLC on mice as measured by their body weight. Mice which have a toxic dose of poly ICLC will experience signs, such as rapid loss in body weight, piloerection and decreased body movement. Mice were administered two daily doses of 30 μg/animal of free poly ICLC. Referring to FIG. 2, the first dose was given at day −2 post drug administration and the second dose was given at day 0 post drug administration. It was found that mice were loosing up to 2 g (close to 10% of total body weight) within 1–3 days after each administration. In addition to the loss of body weight, these mice also showed abnormal symptoms or signs of piloerection (ruffled fur) and decreased body movement. In contrast, mice given identical doses of the liposome-encapsulated poly ICLC did not have significant loss of body weight, nor did they show any signs of piloerection and loss of movement. Therefore, it was found that free unencapsulated poly ICLC had high toxicity, whereas liposome-encapsulated poly ICLC had a low toxicity as shown from the results in FIG. 2. The mice which were administered with liposomal poly ICLC did not exhibit a significant loss of body weight.

In conclusion, the results showed that free poly ICLC when administered directly into mice provided limited protection against influenza A virus infection. Moreover, poly ICLC was shown to be very toxic to mice. In contrast, liposome-encapsulated poly ICLC provided effective treatment against viral infections by enhancing the therapeutic efficacy while decreasing the toxicity of poly ICLC.

I claim:

1. A method of prophylactically treating an influenza viral infection in a mammal comprising administering to said mammal a composition comprising polyriboinosinic and polyribocytidylic acids stabilized in poly-L-lysine and carboxymethylcellulose encapsulated within liposomes.

2. A method of prophylactically treating an equine encephamyelitis viral infection in a mammal comprising administering to said mammal a composition comprising polyriboinosinic and polyribocytidylic acids stabilized in poly-L-lysine and carboxymethylcellulose encapsulated within liposomes.

3. A method of claim 1, wherein said liposomes are cationic liposomes comprising phosphatidylcholine, a cationic lipid and cholesterol.

4. A method of claim 2, wherein said liposomes are cationic liposomes comprising phosphatidylcholine, a cationic lipid and cholesterol.

5. A method of claim 3, wherein said cationic lipid is stearylamine.

6. A method of claim 4, wherein said cationic lipid is stearylamine.

7. A method of claim 3, wherein said phosphatidylcholine, cationic lipid and cholesterol are present in a molar ratio of 9:1:1, respectively.

8. A method of claim 4, wherein said phosphatidylcholine, cationic lipid and cholesterol are present in a molar ratio of 9:1:1, respectively.

9. A method of claim 5, wherein said phosphatidylcholine, stearylamine and cholesterol are present in a molar ratio of 9:1:1, respectively.

10. A method of claim 6, wherein said phosphatidylcholine, stearylamine and cholesterol are present in a molar ratio of 9:1:1, respectively.

11. A method of any of claim 1, 3, 5, 7, or 9 wherein said administering comprises intranasal administration.

12. A method of any of claim 1, 3, 5, 7 or 9 wherein said administering comprises intraperitoneal administration.

13. A method of any of claim 1, 3, 5, 7 or 9 wherein said administering comprises intravenous administration.

14. A method of any of claim 2, 4, 6, 8, or 10 wherein said administering comprises intranasal administration.

15. A method of any of claim 2, 4, 6, 8 or 10 wherein said administering comprises intraperitoneal administration.

16. A method of any of claim 2, 4, 6, 8 or 10 wherein said administering comprises intravenous administration.

17. A method of any of claim 1, 3, 5, 8 or 9 wherein said administering comprises administration by inhalation.

18. A method of any of claim 2, 4, 6, 8 or 10 wherein said administering comprises administration by inhalation.

* * * * *